United States Patent
Kellum et al.

(10) Patent No.: US 11,629,370 B2
(45) Date of Patent: *Apr. 18, 2023

(54) DETECTION OF BACTERIA USING BACTERIOPHAGE

(71) Applicants: University of Pittsburgh - Of the Commonwealth System of Higher Education, Pittsburgh, PA (US); Duquesne University of the Holy Spirit, Pittsburgh, PA (US)

(72) Inventors: John Alston Kellum, Pittsburgh, PA (US); John D. Hempel, North Braddock, PA (US); Robert Hugh Edgar, Pittsburgh, PA (US); John Andrew Viator, Pittsburgh, PA (US)

(73) Assignees: University of Pittsburgh—Of the Commonwealth System of Higher Education, Pittsburgh, PA (US); Duquesne University of the Holy Spirit, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/202,886

(22) Filed: Mar. 16, 2021

(65) Prior Publication Data

US 2021/0262001 A1 Aug. 26, 2021

Related U.S. Application Data

(60) Continuation of application No. 16/720,924, filed on Dec. 19, 2019, now Pat. No. 10,961,557, which is a division of application No. 15/748,490, filed as application No. PCT/US2016/044621 on Jul. 29, 2016, now Pat. No. 10,544,443.

(60) Provisional application No. 62/199,472, filed on Jul. 31, 2015.

(51) Int. Cl.
| | | |
|---|---|---|
| *C12Q 1/04* | (2006.01) |
| *G01N 29/24* | (2006.01) |
| *G01N 15/10* | (2006.01) |
| *C12N 7/00* | (2006.01) |
| *C12N 7/02* | (2006.01) |

(52) U.S. Cl.
CPC ............ *C12Q 1/04* (2013.01); *C12N 7/00* (2013.01); *C12N 7/02* (2013.01); *G01N 15/10* (2013.01); *G01N 29/2425* (2013.01); *C12N 2795/10321* (2013.01); *C12N 2795/10331* (2013.01); *G01N 2015/1006* (2013.01); *G01N 2291/02466* (2013.01)

(58) Field of Classification Search
None
See application file for complete search history.

(56) References Cited

U.S. PATENT DOCUMENTS

| | | |
|---|---|---|
| 4,797,363 A | 1/1989 | Teodorescu |
| 2001/0006783 A1 | 7/2001 | Nogami |
| 2008/0241819 A1 | 10/2008 | Smith |
| 2009/0170149 A1 | 7/2009 | Viator |
| 2011/0097702 A1 | 4/2011 | Voorhees |

FOREIGN PATENT DOCUMENTS

| | | |
|---|---|---|
| EP | 16833591.7 | 2/2019 |
| JP | S60159648 A | 8/1985 |
| WO | WO2005100612 A2 | 10/2005 |
| WO | WO2017023721 | 2/2017 |

OTHER PUBLICATIONS

Schmelcher, Mathias et al., Application of bacteriophages for detection of foodborne pathogens, Bacteriophage, vol. 4, e28137, (2014), pp. 1-14.

Mosier-Boss, P.A. et al., Use of fluorescently labeled phage in the detection and identification of bacterial species, Applied Spectroscopy, vol. 57, No. 9, (2003), pp. 1138-1144.

*Primary Examiner* — Brian Gangle

(74) *Attorney, Agent, or Firm* — Bartony & Associates, LLC

(57) ABSTRACT

A method of detecting a species, strain or type of bacteria includes mixing a labeled bacteriophage including a label that is detectible via a detection system with a bacterial culture including the species, strain or type of bacteria to which the labeled bacteriophage selectively binds and using the detection system to detect the labeled bacteriophage bound to the species, strain or type of bacteria.

10 Claims, 4 Drawing Sheets

DETECTION OF BACTERIA USING BACTERIOPHAGE

CROSS-REFERENCE TO RELATED APPLICATIONS

This application is a continuation of U.S. patent application Ser. No. 16/720,924, filed Dec. 19, 2019, which is a divisional patent application of U.S. patent application Ser. No. 15/748,490, filed Jan. 29, 2018, now U.S. Pat. No. 10,544,443, which is a national phase filing of PCT International Patent Application No. PCT/US2016/044621, filed Jul. 29, 2016, which claims benefit of U.S. Provisional Patent Application Ser. No. 62/199,472, filed Jul. 31, 2015, the disclosures of which are incorporated herein by reference.

GOVERNMENTAL INTEREST

This invention was made with government support under grant no. CA182840 awarded by the National Institute of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Current methods for isolating bacteria from, for example, body fluids (such as blood) require 48 hours or longer in a hospital, laboratory or other setting to determine the exact species, strain or type of bacteria present. Moreover, those methods are unable to quantify accurately any detected bacteria and are limited to those that readily grow on an agar plate. A quicker, quantitative assay or test would be highly beneficial.

SUMMARY

In one aspect, a method of detecting or determining a species, strain or type of bacteria includes mixing a labeled bacteriophage including a label that is detectible via a detection system with a bacterial culture including the species, strain or type of bacteria to which the labeled bacteriophage selectively binds and using the detection system to detect the labeled bacteriophage bound to the species, strain or type of bacteria. The method may, for example, further include removing unbound labeled bacteriophage after mixing the labeled bacteriophage with the bacterial culture. In a number of embodiments, the detection system comprises a photoacoustic cell. The detection system may, for example, include a photoacoustic flowmetry system. The species, strain or type of bacteria may be identified and quantified. In a number of embodiments, the level of energy used in a photoacoustic system (or a system including a photoacoustic cell) is sufficiently low to reduce, minimize or eliminate detection of unbound labeled bacteriophage. In that regard, by binding to a target bacterium, the bacteriophage become spatially-sequestered, thus enhancing the signal their tag produces.

In a number of embodiments, a plurality of labeled bacteriophages may be mixed with the sample. Each of the plurality of bacteriophages selectively binds with a different species, strain or type of bacteria. Each of the plurality of bacteriophages includes a different label that is separately detectable via the detection system. The detection system is used to determine the presence of the labeled bacteriophage bound to at least one of the different species, strains or types of bacteria. The bacteriophages may, for example, be labeled with different labels that are detectible at different wavelengths of energy.

In another aspect, a system for determining if a sample includes at least one species, strain or type of bacteria, includes a plurality of bacteriophages. Each of the plurality of bacteriophages selectively binding with a different species, strain or type of bacteria. Each of the plurality of bacteriophages including a different label that is separately detectable via a detection system.

In another aspect, a system for detecting a species, strain or type of bacteria includes a labeled bacteriophage, which binds selectively to the species, strain or type of bacteria and includes a label attached thereto, and a system adapted to detect the labeled bacteriophage bound to the species, strain or type of bacteria. The detection system may, for example, include a photoacoustic cell. In a number of embodiments, the detection system includes a photoacoustic flowmetry system. As described above, the species, strain or type of bacteria may be identified and quantified.

In a further aspect, a bacteriophage includes a label attached thereto, wherein the label is selected to be detectible via a detection system. The label may, for example, be detectible using a photoacoustic cell. In a number of embodiments, the label is detectible using a photoacoustic flowmetry system.

The present devices, systems, methods and compositions, along with the attributes and attendant advantages thereof, will best be appreciated and understood in view of the following detailed description taken in conjunction with the accompanying drawings.

DETAILED DESCRIPTION

Figure 1:
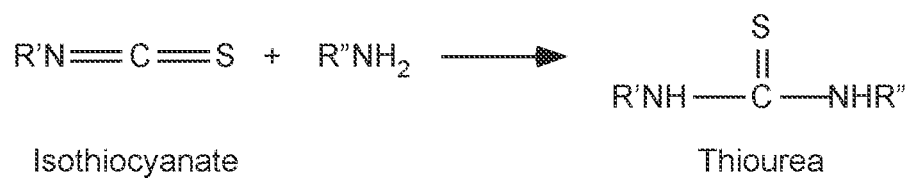
FIG. 1 illustrates a representative scheme for labeling or tagging a bacteriophage with a label including an isothiocyanate moiety (fluorescein isothiocyanate).
Figure 1:
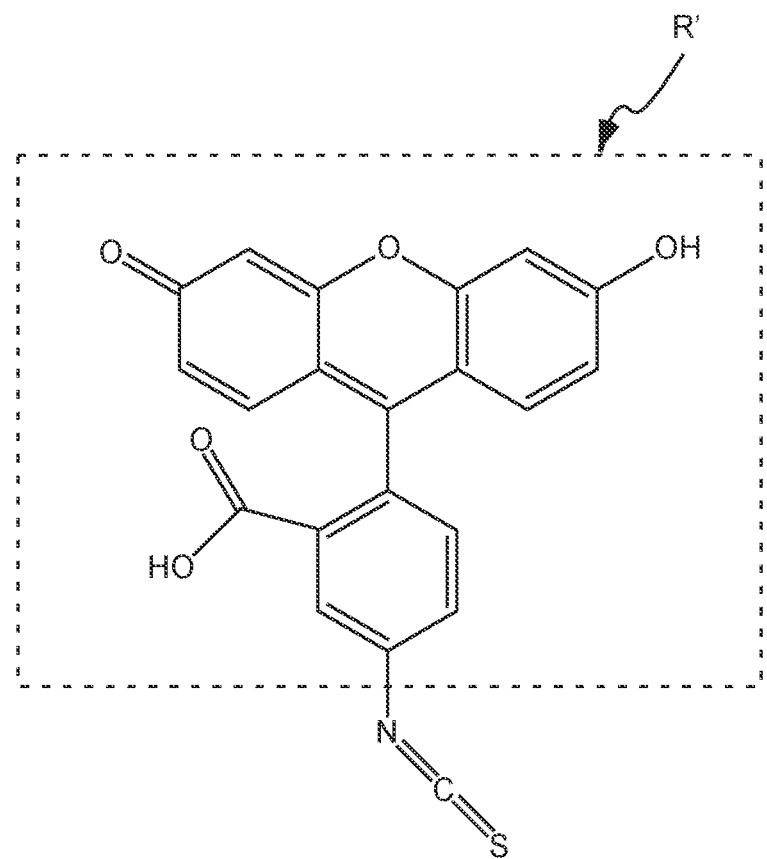

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a bacteriophage" includes a plurality of such bacteriophages and equivalents thereof known to those skilled in the art, and so forth, and reference to "the bacteriophage" is a reference to one or more such bacteriophages and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

Bacteriophages (sometime referred to as phages) are viruses that infect bacteria by discriminately binding to externally presented surface antigens of their target bacterial hosts. In a number of embodiments, devices, systems and methods hereof provide rapid bacterial typing assay using a sensing system (for example, a photoacoustic sensing system) and labeled bacteriophages. The terms "label" and "tag" are used herein interchangeably to refer to an entity or moiety that is associable with a bacteriophage and that can be detected via a detection system. In that regard, bacteriophages or phages are labeled or tagged using a detectible label or tag (for example, a photoacoustic labile label or tag) and then added to, for example, bacterial mixtures or cultures of target and non-target bacteria. As used herein, the term "labile" refers to labels or tags which may be easily changed and/or the same label or tag may be used with a variety of bacteriophages. A wash step may, for example, be used to remove excess and unbound phage after phage absorption. The labeled or tagged phage/bacterial mixture is then processed through a detection system (such as a photoacoustic cell) where targeted bacterias are detected by the attached labeled or tagged phage.

Photoacoustics is the transduction of photons into mechanical energy by targeting light absorbing objects with rapid pulsed laser light. Photoacoustic waves may, for example, be generated by thermoelastic expansion, that is laser induced heating, resulting in volume expansion and contraction.

Studies of a number of embodiments hereof have demonstrated the feasibility of the present approach with, for example, a spiked culture with a signal to noise ratio in excess of 5/1. The studies hereof demonstrate that bacteriophage can be effectively used to determine bacterial contamination in a mixed culture. Moreover, the studies hereof demonstrate the value of expanding detection capabilities by using additional phages with varying host ranges targeting, for example, both gram negative and gram positive human pathogens. The devices, systems and methods hereof provide a clinically accessible method to determine bacterial contamination and lower the time required to obtain results (as compared to present detection methodologies) by at least one order of magnitude (for example, results within 3-4 hours rather than 3-4 days). An assay with such capabilities may be very advantageous in, for example, hospitals and medical laboratories. Incorporating assays hereof may, for example, allow doctors to treat infections earlier using, for example, targeted antibiotics. The impact of such advancement in detection techniques would be likely to support future tailored phage therapy and have a significant and global lifesaving potential.

Host ranges for a variety of bacteriophages have been determined previously. Additionally, bacterial host range has been shown to be primarily determined by phage binding to bacterial O-antigens and other surface proteins presented by the bacteria. As set forth above, bacteriophage are viruses that infect bacteria. The host range of a bacteriophage is defined by which bacterial genera, species and strains or types the bacteriophage can infect and lyse. The host range of a bacteriophage is one of the defining biological characteristics of a particular bacterial virus. Productive phage infection requires: 1. successful host attachment, 2. initial penetration of the host outer membrane and/or cell wall, 3. transfer of the phage DNA through the inner membrane leading to synthesis of phage-encoded proteins and nucleic acid, and 4. escape of progeny phage from the dead host cell (lysis). Host attachment is mediated by specialized proteins called tail spikes and tail fibers presented on the posterior tip of tailed phages. These proteins attach to specific structures on the outer surface of host bacteria. Lipopolysaccharides (O-antigens), flagellin, teichoic acids, capsular polysaccharides (K-antigens), and specific membrane proteins such as nutrient transporters can be used as attachment sites. The ability of a phage to attach to specific cell surface molecules is considered the primary determinant of host range. There are other physiological or genetic properties of cells that influence the ability of certain phage to replicate in them, for example the presence of a restriction enzyme or a CRISPR system, and these can in principle influence host range. Bacteriophage host range and bacterial resistance is, for example, discussed in Hyman P1, Abedon ST, *Adv Appl Microbiol*.m 2010; 70:217-48. doi: 10.1016/S0065-2164 (10)70007-1. Epub 2010 Mar. 6; and Kutter, E. *Methods Mol Biol.,* 2009; 501:141-9. doi: 10.1007/978-1-60327-164-6_14.

By using, for example, a photoacoustic cell or other detection system, one may use a bacteriophage's ability to discriminately or selectively bind to further discriminate the bacteria. In that regard, a labeled or tagged (for example, photoacoustic labeled or tagged) bacteriophage allows one to detect or identify specific bacteria to which the labeled bacteriophage selectively binds. Labels and associated detection systems other than photoacoustic detections system (such as flow cytometry, using a fluorescent label or tag), or electron microscopy may be used in a number of embodiments hereof. In flow cytometry, a bacteriophage may, for example, have a fluorescent molecule bound to the bacteriophage using an intermediary binding agent (for example, monoclonal antibody to phage and green fluorescent protein or GFP bound to antibody). Electron microscopy may, for example, be used wherein nano-gold particles may be attached to bacteriophage, targeted to bacteria, stained, and counted using an electron microscope. In general, photoacoustic sensing or detection systems may provide increased detection rates and specificity over many other detection systems (for example, flow cytometry and or electron microscopy) at a reduced cost.

In a number of studies hereof, a photoacoustic compatible or photoacoustic label/tag was first bound to bacteriophage. A photoacoustic tag or label as used herein refers to any compound or moiety that provides a photoacoustic signal. Such compounds can be determined in the literature, via experimentation, or via theory. In a number of embodiments, photoacoustic tags or labels suitable for use herein are readily incorporated into or bound to the bacteriophage and do not interfere significantly with the binding activity of the bacteriophage. Examples of suitable photoacoustic tags or labels include, but are not limited to, fluorescein isothiocyanate (FITC; available, for example, from Sigma-Aldrich of St. Louis, Mo. USA), Evans blue dye (EB; an azo dye having the formula $C_{34}H_{24}N_6Na_4O_{14}S_4$; available, for example, from Sigma-Aldrich), IR775S, Blue (a cyanine dye derivative) and the protein dye Direct Red 81 ($C_{29}H_{19}N_5Na_2O_8S_2$; available, for example, from Sigma-Aldrich). Direct Red 81 and many other tags or labels may be used with many different bacteriophages and do not interfere with the activity of the bacteriophage, was used in studies hereof. In general, virtually any tag or label (for example, a tag or label detectible via a photoacoustic signal) can be used in connection with any bacteriophage. There is also an almost unlimited variety of tags that may be used. Because of the chemistry of such labels, labeling the bacteriophage may be as simple as mixing the bacteriophage with the label.

Many techniques known to those skilled in the art are suitable for attachment of labels or tags to bacteriophages. Fluorescein isothiocyanate forms covalent adducts with amino groups. With proteins, the epsilon-amino groups of lysine residues may provide the amino groups. The capsid proteins of the bacteriophages provide lysine residues for reaction. FIG. 1 illustrates an example of a reaction scheme for the reaction of an amino group with an isothiocyanate. FIG. 1 also illustrated the chemical structure of fluorescein isothiocyanate. In the scheme of FIG. 1, R' is the fluorescein moiety and R" is the target protein with $NH_2$ being the epsilon amine of a lysine residue of that protein. Further, many dye compounds suitable for use as labels herein, contain sulfonic acid ($SO_3$) groups. The pKa of these sulfonic acid groups is sufficiently low that they afford extremely tight binding with basic groups provided by lysine and arginine residues in proteins, especially at the relatively neutral pH and ionic strengths used in the tests (assays) hereof.

In a number of embodiments, a preparation of a single bacteriophage with a known host range was titered to determine specifically and accurately the number of infectious particles/ml. The photoacoustic label was bound to phage by incubating phage with an excess of the label. Labeled bacteriophage were then pelleted using a desktop centrifuge and re-suspended in fresh buffer to remove any unbound label. Labeled phage were titered to determine the number of infectious particles/ml. The number of infectious particles/ml pre- and post-labeling was indistinguishable, demonstrating that labeling of phage particles did not decrease or change their rate of infectivity. In several representative embodiments hereof, labeled Det7 bacteriophage was bound to LT2 *Salmonella*, labeled HK97 was bound to LE392 *E. coli*, D29 bacteriophage was used in connection with k12 *E. coli* as a negative control (D29 is a mycobacterium bacteriophage and does not attach to *E. coli*), and labeled T4 bacteriophage was bound to *E. coli* B and K12 *E. coli* and *Serratia*.

As described above, in a number of studies, the labeled phage was detected using photoacoustic labels or tags. In that regard, labeled bacteriophages with a known titer from the previous studies were collected in fresh buffer. Phages were pelleted using a desktop centrifuge and re-suspended in fresh buffer with no photoabsorbance. Phages were re-suspended to give a known number of labeled particles/ml. The phage buffer mixture was then titered through the photoacoustic cell to determine the number of labeled phages needed for detection. Labeled phages were detected, demonstrating that signal from labeled unbound phages was detectable by the photoacoustic cell.

The labeled phage was then tested with target bacteria. In a number of studies, host bacteria of labeled phages were titered to determine the colony forming units/ml. Labeled phages from previous studies of a known titer were added in a 10 to 1 ratio of phage to target bacteria. The phage/bacteria mixture was incubated together for a set period of time to allow the phages to bind to the bacteria. The phage/bacteria mixture was then pelleted using a desktop centrifuge and re-suspended in an equal volume of fresh buffer to remove any unbound labeled phages. Bacteria with bound labeled phages were then run through the photoacoustic cell and signal detected. Unbound bacteria alone were run as a negative control.

Figure 2:
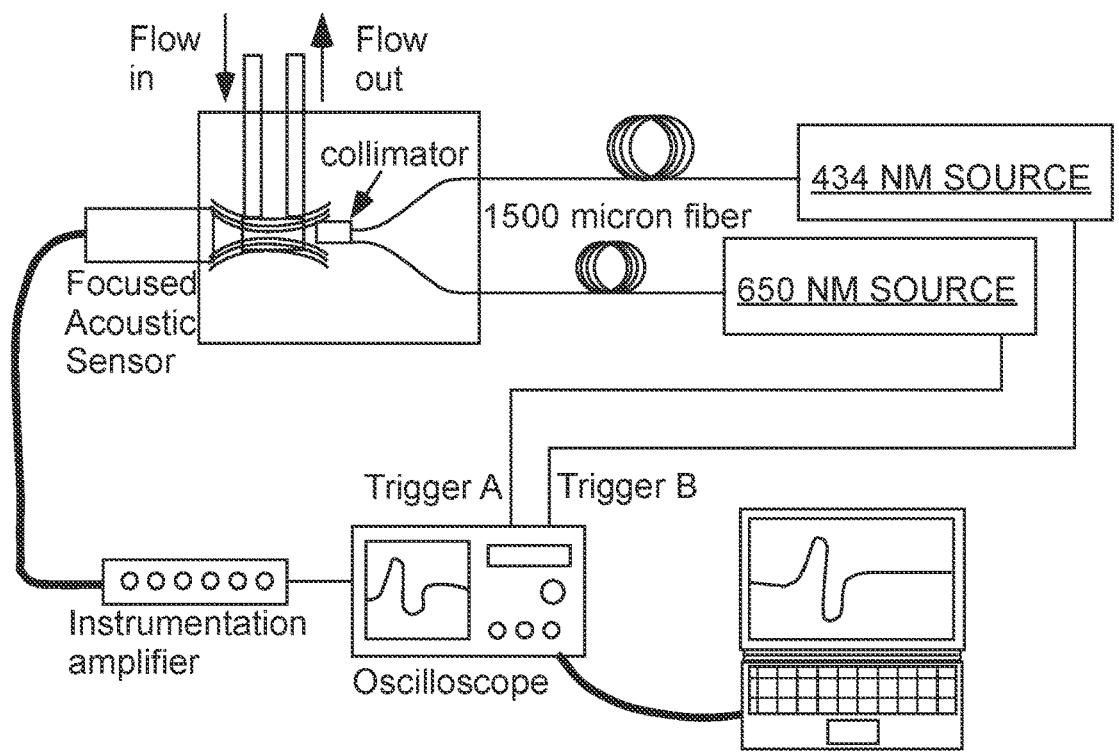
FIG. 2 illustrates an embodiment of a photoacoustic flowmetry system.
Figure 3:
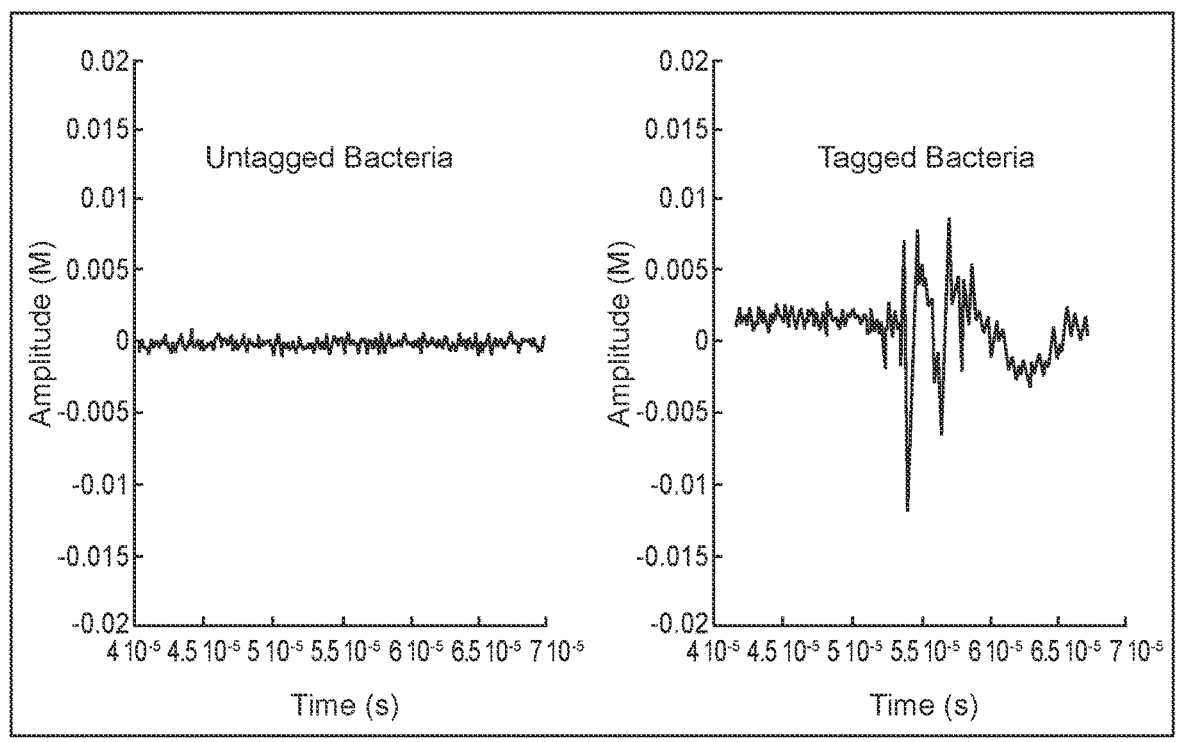
FIG. 3 illustrates a study of the use of labeled or tagged bacteriophage to detect a specific bacteria using a photoacoustic flowmetry system showing that untagged bacteria do not provide a photoacoustic signal whereas tagged bacteria (via the tagged bacteriophage) provide a photoacoustic signal.

FIG. 2 illustrates a representative embodiment of a photoacoustic flowmetry system. In one study, a rapid bacterial typing assay hereof used photoacoustic flow cytometry- or laser induced ultrasound, in which 532 nm laser light generated ultrasonic waves in phage containing a photostable chromophore. Bacteriophages were labeled using a photoacoustic labile tag and then added to bacterial cultures of target and non-target bacteria as described above. Once again, excess and unbound phage was removed after bacterial absorption using centrifugation. Labeled phage/bacterial mixture was then processed through a microfluidic system in which 5 ns pulsed laser light generated high frequency ultrasonic waves in the targeted bacterial cells as a result of thermoelastic expansion in the dye particles. The photoacoustic flowmeter contained a focused ultrasound transducer that detected the ultrasonic waves generated in target bacteria. This signal (see, for example, FIG. 3) was processed and stored in a computer using an automated software interface. Bacterial cells providing a positive signal were charted against the total number of cells processed to obtain an absolute number of each target bacteria cell in the culture. Using *E. coli*, for example, a signal to noise ratio in excess of 5:1 was achieved. The studies hereof demonstrated that bacteriophages—coupled with a detection scheme such as photoacoustics may be effectively used to quantify specific bacteria in a mixed culture.

Figure 4:
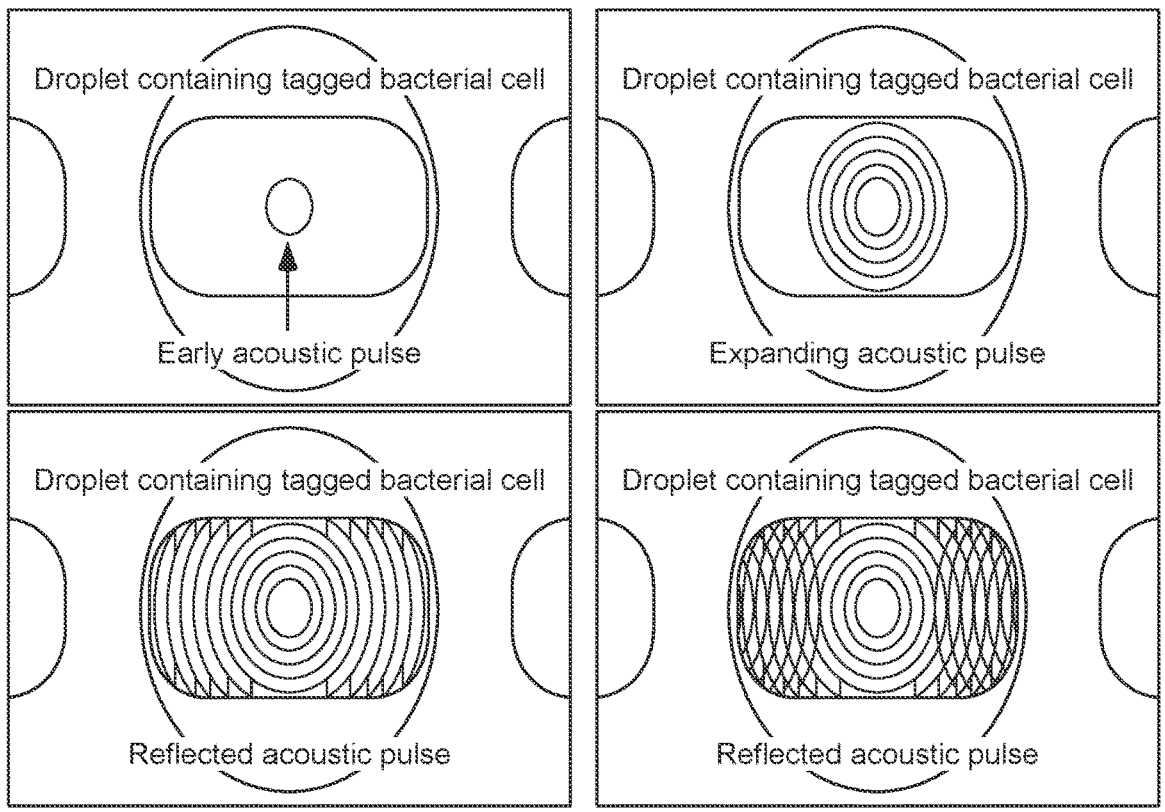
FIG. 4 illustrates a representation of isolation of target bacterial cells using two phase flow.
Figure 5:
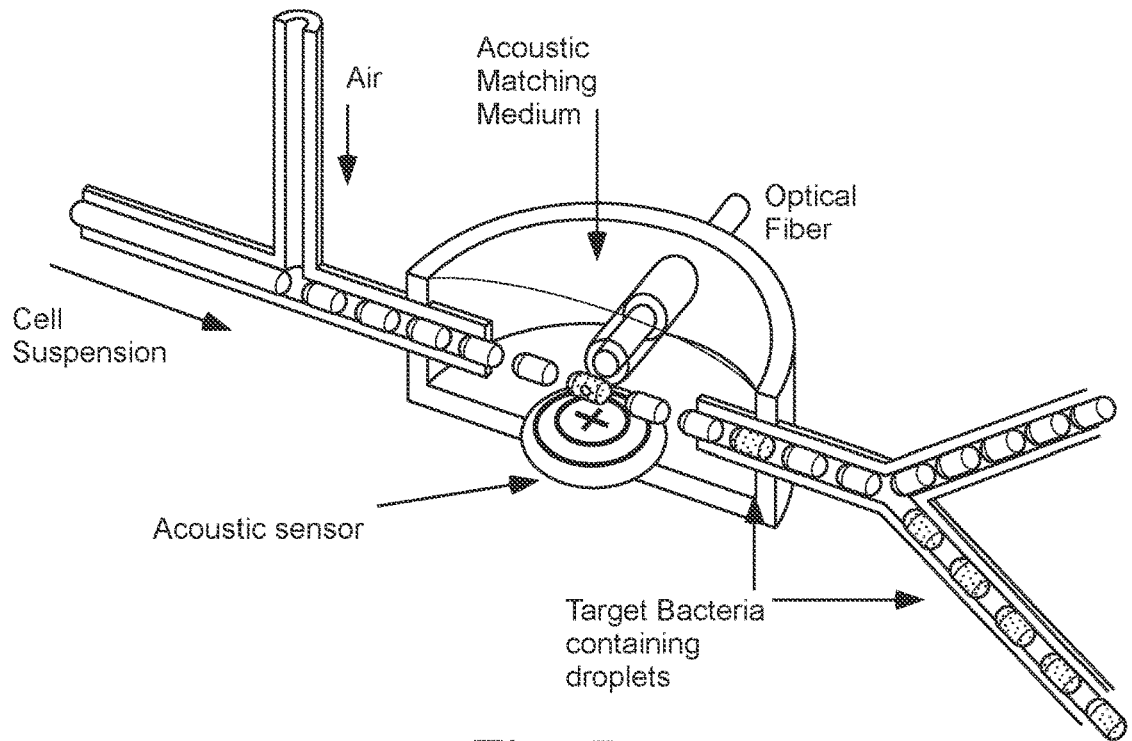
FIG. 5 illustrates another representation of isolation of target bacterial cells using two phase flow.

FIG. 4 illustrates progression of thermoelastic expansion caused by laser pulse inside each droplet during photoacoustic detection. FIG. 5 illustrates a view of photoacoustic cell using two phase flow. The sample flows through the photoacoustic cell one droplet at a time. Each droplet is impinged with light from the laser, and a signal is detected by the acoustic sensor (not shown, but may, for example, be positioned directly under the photoacoustic cell).

Figure 6A:
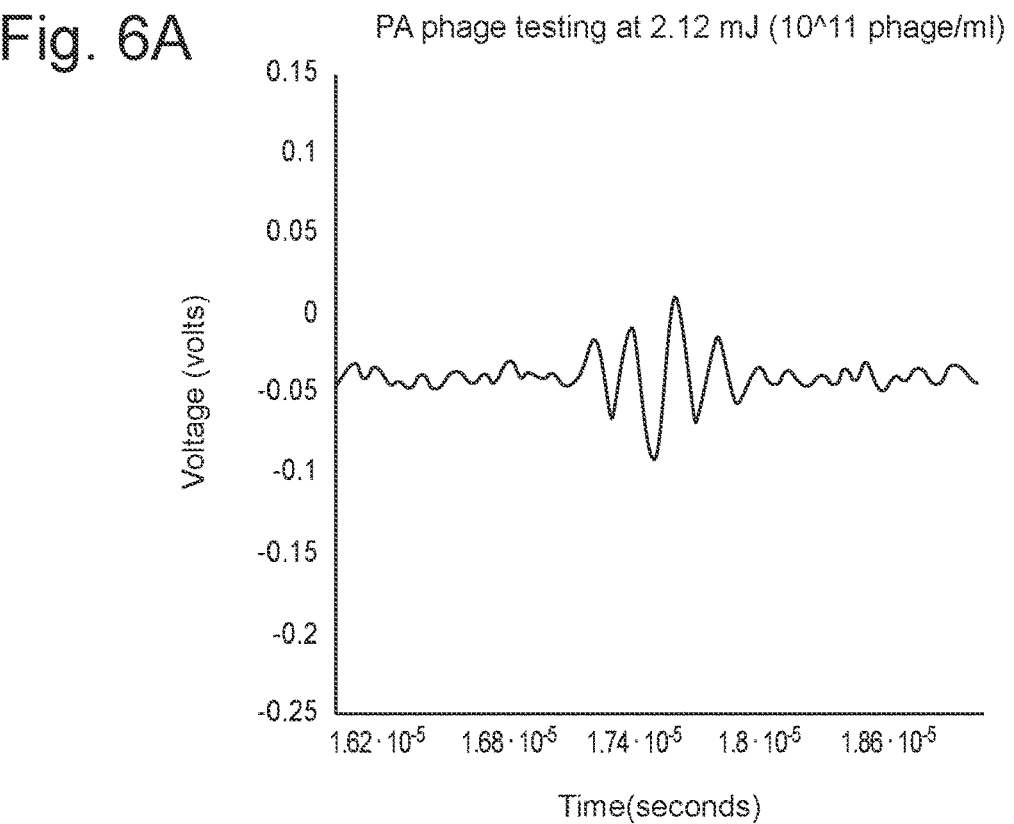
FIG. 6A illustrates a waveform resulting from laser irradiation of bacteriophage at about 2.12 millijoules (mJ) per pulse.
Figure 6B:
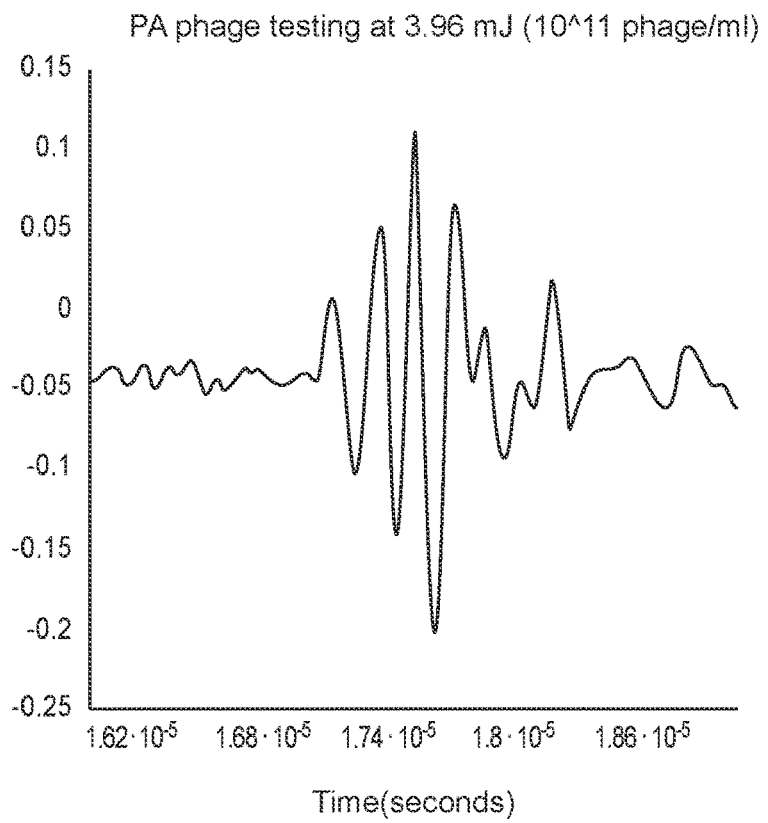
FIG. 6B illustrates a waveform resulting from laser irradiation of bacteriophage at about 3.96 mJ per pulse.

FIGS. 6A and 6B illustrate two graphs of photoacoustic waveforms from irradiating free-floating or unbound phage. The waveform of FIG. 6A, results from laser irradiation of bacteriophage at about 2.12 millijoules (mJ) per pulse. The waveform of FIG. 6B results from irradiation of bacteriophage at 3.96 millijoules (mJ) per pulse. These results indicated that in embodiments of detection algorithms hereof, use of sufficiently low energy (for example, approximately 2 mJ) irradiation results in waveforms that are below a predetermined detection threshold. A suitable level of energy for irradiation is readily determined by one skilled in the art. Bacteriophage that are bound to bacteria will be more concentrated and will give larger amplitude signals. Beneficially, any free-floating phage will not be detected in a detection protocol with sufficiently low energy.

A demanding challenge for clinicians is to correctly identify patients who are most likely to benefit from empiric treatment with broad-spectrum antibiotics with activity against multi-drug resistant pathogens. These antibiotics are more expensive and carry a greater toxicity than standard regimens. In addition, the use of broad-spectrum antibiotics for patients who could be treated with narrower-spectrum drugs results in emergence of drug resistance in the community and further complicates management. The ability to exclude organisms with a risk of drug resistance would allow the use of cheaper, safer antibiotics for many patients now treated with empiric broad-spectrum therapy.

Two scenarios confound diagnosis of bacterial infections. First, some bacteria are hard or even impossible to grow in culture. For example, common pathogens in pneumonia such as *Mycoplasma pneumoniae* do not grow in culture. Second, even organisms that can routinely be cultured will not grow in the presence of antibiotics (that may have been given to the patient empirically). Resins that can remove antibiotics from the sample are sometimes effective but often all therapy must be stopped for a period of time and then the patient's blood or other fluids can be cultured. This delays management and may put the patient at risk.

When non-sterile fluids are cultured (e.g. sputum) there is often a need to estimate the number of bacteria present in order to distinguish flora from pathogen. The usual approach is to use serial dilutions to "plate out" organisms and count the colonies. This a slow process that can require days to obtain a result. Phage-based detection as described herein has the ability to estimate the number of organisms in a sample in a single step, taking, for example, hours rather than days.

In a representative clinical example, a patient presents with cough, high fever and a chest radiograph showing a lobar infiltrate. The standard approach to management would be to use broad-spectrum antibiotics to cover a variety of pathogens and send samples of blood and sputum for culture. The disadvantages of this approach include: (i.) multiple antibiotics or "super antibiotics" are needed introducing higher cost and greater risk for side effects; (ii.) ability to "cover" only about 85-90% and thus treatment may be ineffective in 10-15% of cases leading to delay in adequate antibiotics and increased risk of death; and (iii.) initial cultures are only positive in about 50% of cases (or less) and subsequent cultures may fail because antibiotics are on board and will be in the sample, leading to a diagnostic change and increased risk for adverse outcomes.

By contrast, the approach of a representative embodiment of the present methodology is shown in the Table 1 below. In Table 1, NA is not applicable and BSA is a broad-spectrum antibiotics (for example, piperacillin tazobactam). In the example of Table 1, the different labeled phages (that is, including labels with different/separately detectable or measurable detection characteristics/wavelengths) could be applied concurrently to the sample.

TABLE 1

| Bacteria | Phage | Label | Wavelength | Comment | Treatment |
|---|---|---|---|---|---|
| Pneumococcus | SV1 | Trypan Blue | 430 | Difficult to grow in culture | Ampicillin |
| *Staphylococcus* | NA81 | Direct Red 81 | 532 | May be methicillin resistant | Vancomycin |
| *Haemophilus* Inf. | HP2 | Methylene Blue | 605 | May be resistance to ampicillin | Ceftriaxone |
| *Mycoplasma* | MFV1 | Indocyanine Green | 670 | Does not grow in culture | Erythromycin |
| *Legionella* | ΦLP6 | India Ink | 800 | Does not grow in culture | Erythromycin |
| Other bacteria | NA | | Null | Most other bacteria will grow | BSA |
| None | NA | | Null | Viruses and fungi are rare causes | No antibiotics* |

In the example of Table 1, a sample showing a photoacoustic signal from an excitation laser wavelength of 430 nm would be interpreted as positive for pneumococcal pneumonia (the most common pathogen) and would allow the use of a low cost, low-toxicity single drug regimen (ampicillin). Conversely a photoacoustic signal from an excitation laser wavelength of 532 nm would lead to a diagnosis of *staphylococcus*. This organism is commonly resistant to ampicillin (and other penicillin-like drugs) and so vancomycin would be used. The treatment of viral or fungal pneumonia with antibiotics can actually cause harm. Further workup for rare causes including tuberculosis would be facilitated by early recognition that a "rare cause" is present. A result of "null" would lead clinicians to either suspect unusual bacteria or (more commonly) viral infection. Importantly, a null result from the test hereof and "no growth" result from culture (available in 24 hours) would lead to a highly likely viral diagnosis, and antibiotics could be withheld. The bacteriophages listed in Table 1 are only representative phages for each bacteria. As known to those skilled in the art, there are numerous other bacteriophages that could be used in connection with each of the listed bacteria.

Experimental

Representative protocol for bacteriophage binding. In a representative example, the bacteriophage was HK97 as $10^{10}$ plaque forming units per ml (pfu/ml). The bacteria was Ymel *E. coli* at $10^9$ colony forming units per ml (cfu/ml). The culture could be stored at 4° C. for approximately 1 week. For incubation, 10-100 bacteriophage were added per bacterial cell. The mixture was incubated for 5-10 minutes at 37° C. with shaking. Incubation with water at 37° C. with gentile agitation is also acceptable. The cell/bacteriophage mixture was placed in an eppindorf tube and spun 10,000×g for 1-2 minutes. The supernatant (containing unbound phage) was poured off. The pellet was resuspended in equal volume of chilled phosphate buffer solution (PBS), luria broth (LB), or sterile water. Infected cells will have 20-60 minutes before lysis starts to occur.

Representative protocol for labeling bacteriophage and unbound bacteriophage studies. 100 µl of purified bacteriophage (10" pfu/ml final concentration) was added to 900 µl of direct red solution at a concentration of 100 µg/ml. The bacteriophage was incubated at room temperature for 30 minutes after vortexing. The bacteriophage was then pelleted using a refrigerated centrifuge (for example, for 3 hours at 14,800×g at 4° C. The supernatant was removed and the pellet was washed with PBS at a pH OF 7.2 (10" pfu/ml).

In the photoacoustic studies of the bacteriophage at 2.12 mJ (see FIG. 6A), a 1 ml sample was run through the photoacoustic system with laser energy at 2.12 mJ. In 23 detections, 11 were greater than the threshold level. Constant low-level detection was just below the threshold. The signal from low-level detection disappeared when water was run subsequently through the system. The sample was collected and used for the next experiment. The recovered sample was tittered and found to still be 10" pfu/ml. The few detections that were above threshold level were likely a result of clumped bacteriophage.

In the photoacoustic studies of the bacteriophage at 3.96 mJ, the laser energy was increased to 3.96 mJ (see FIG. 6B). Water was run through the system to test background. In running the bacteriophage sample through the system, constant detection, well above the threshold, was achieved. Water was run through the system directly after detection of bacteriophage and the signal disappeared completely.

These results indicated that aggregated bacteriophage can be detected at a lower energy level (for example, approximately 2 mJ). The bacteriophage will be aggregated using target bacteria. At such lower energy levels, however, unbound phage will not be detected.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of determining if a sample taken from a patient includes a species, strain or type of bacteria, comprising: mixing a labeled bacteriophage including a label that is detectible via a detection system with the sample, the labeled bacteriophage being active to selectively bind with the species, strain or type of bacteria, applying light energy to the sample to generate photoacoustic waves, and measuring the generated photoacoustic waves to determine the presence of the labeled bacteriophage bound to the species, strain or type of bacteria.

2. The method of claim 1 further comprising removing unbound labeled bacteriophage after mixing the labeled bacteriophage with the sample.

3. The method of claim 1 wherein the light energy is applied to the sample and the generated photoacoustic waves are measured via a detection system comprising a photoacoustic cell.

4. The method of claim 3 wherein the detection system comprises a flowmetry system.

5. The method of claim 1 wherein the species, strain or type of bacteria is quantified upon detection.

6. The method of claim 3 wherein the level of light energy used in the photoacoustic cell is sufficiently low to reduce detection of unbound labeled bacteriophage.

7. The method of claim 1 wherein a plurality of labeled bacteriophages are mixed with the sample, each of the plurality of bacteriophages selectively binding with a different species, strain or type of bacteria, each of the plurality of bacteriophages including a different label that is separately detectable.

8. The method of claim 7 further comprising removing unbound labeled bacteriophage after mixing the labeled bacteriophage with the sample.

9. The method of claim 7 wherein the light energy is applied to the sample and the generated photoacoustic waves are measured via a detection system comprising a photoacoustic cell and the level of energy used in the photoacoustic cell is sufficiently low to reduce detection of unbound labeled bacteriophage.

10. The method of claim 9 wherein the detection system comprises a photoacoustic flow cytometry system.

* * * * *